United States Patent
Oakhill

(10) Patent No.: US 9,833,188 B2
(45) Date of Patent: Dec. 5, 2017

(54) SYSTEMS AND METHODS FOR BEDDING WITH SLEEP DIAGNOSTICS

(71) Applicant: Dreamwell, Ltd., Las Vegas, NV (US)

(72) Inventor: Timothy Oakhill, Atlanta, GA (US)

(73) Assignee: DREAMWELL, LTD., Las Vegas, NV (US)

( * ) Notice: Subject to any disclaimer, the term of this patent is extended or adjusted under 35 U.S.C. 154(b) by 200 days.

(21) Appl. No.: 14/802,385

(22) Filed: Jul. 17, 2015

(65) Prior Publication Data

US 2015/0320354 A1    Nov. 12, 2015

Related U.S. Application Data

(63) Continuation of application No. 13/015,399, filed on Jan. 27, 2011.
(Continued)

(51) Int. Cl.
*A61B 5/00* (2006.01)
*G06F 19/00* (2011.01)
(Continued)

(52) U.S. Cl.
CPC ............ *A61B 5/4815* (2013.01); *A47C 31/00* (2013.01); *A61B 5/0022* (2013.01);
(Continued)

(58) Field of Classification Search
None
See application file for complete search history.

(56) References Cited

U.S. PATENT DOCUMENTS 5,479,939 A    1/1996  Ogino
5,964,720 A  * 10/1999  Pelz .............................. 600/595
(Continued)

FOREIGN PATENT DOCUMENTS

EP        2278508 A1    1/2011
WO    2008096307 A1    8/2008
(Continued)

OTHER PUBLICATIONS

International Search Report, issued in International Application No. PCT/US2011/022778, dated Nov. 5, 2011; 5 pages.
(Continued)

*Primary Examiner* — William Thomson
*Assistant Examiner* — Davin Sands
(74) *Attorney, Agent, or Firm* — Cantor Colburn LLP

(57) ABSTRACT

Systems and methods described herein relate to a sleep diagnostic system including a mattress assembly, a plurality of sensors, data acquisition circuitry, an input device, a sleep processor, and a display device. The mattress assembly may have a sleeping surface, and the plurality of sensors may be disposed within the mattress assembly below the sleeping surface. The sensors are configured to measure at least one sleep condition and output data signals indicative of the sleep condition. The sleep processor receives signals from both the sensors and one or more other input devices, and determines a sleep characteristic based upon these received signals. The display device, which includes circuitry and a graphical user interface, receives the sleep characteristic from the sleep processor and displays it to the user.

25 Claims, 8 Drawing Sheets

Related U.S. Application Data

(60) Provisional application No. 61/299,843, filed on Jan. 29, 2010.

(51) Int. Cl.

| | | |
|---|---|---|
| *A61B 5/0205* | (2006.01) | |
| *A61B 5/11* | (2006.01) | |
| *A47C 31/00* | (2006.01) | |
| *A61B 5/145* | (2006.01) | |
| *A61B 5/024* | (2006.01) | |
| *A61B 5/08* | (2006.01) | |
| *A61M 21/00* | (2006.01) | |
| *A61B 5/01* | (2006.01) | |
| *A61B 5/021* | (2006.01) | |

(52) U.S. Cl.
CPC ........ *A61B 5/0205* (2013.01); *A61B 5/02055* (2013.01); *A61B 5/11* (2013.01); *A61B 5/1112* (2013.01); *A61B 5/1113* (2013.01); *A61B 5/1115* (2013.01); *A61B 5/1118* (2013.01); *A61B 5/14542* (2013.01); *A61B 5/411* (2013.01); *A61B 5/4809* (2013.01); *A61B 5/6891* (2013.01); *A61B 5/6892* (2013.01); *A61B 5/7271* (2013.01); *A61B 5/742* (2013.01); *A61B 5/746* (2013.01); *A61B 5/7475* (2013.01); *G06F 19/3431* (2013.01); *A61B 5/01* (2013.01); *A61B 5/021* (2013.01); *A61B 5/024* (2013.01); *A61B 5/08* (2013.01); *A61B 5/0816* (2013.01); *A61B 2505/07* (2013.01); *A61B 2560/0242* (2013.01); *A61B 2562/046* (2013.01); *A61M 2021/0083* (2013.01)

(56) References Cited

U.S. PATENT DOCUMENTS

| | | | | |
|---|---|---|---|---|
| 6,468,234 | B1 * | 10/2002 | Van der Loos et al. | 600/595 |
| 8,069,512 | B2 * | 12/2011 | Rawls-Meehan | 5/617 |
| 8,458,042 | B1 * | 6/2013 | Roberts et al. | 705/26.1 |
| 2002/0007124 | A1 | 1/2002 | Woodward | |
| 2003/0125899 | A1 * | 7/2003 | Hinshaw et al. | 702/129 |
| 2004/0010202 | A1 * | 1/2004 | Nakatani et al. | 600/529 |
| 2005/0124864 | A1 * | 6/2005 | Mack et al. | 600/300 |
| 2005/0143617 | A1 | 6/2005 | Auphan | |
| 2005/0152378 | A1 | 7/2005 | Bango et al. | |
| 2005/0190065 | A1 * | 9/2005 | Ronnholm | 340/575 |
| 2005/0192508 | A1 * | 9/2005 | Lange et al. | 600/534 |
| 2006/0129047 | A1 | 6/2006 | Ruotoistenmaki | |
| 2006/0152378 | A1 | 7/2006 | Lokhorst et al. | |
| 2006/0224076 | A1 * | 10/2006 | Lange et al. | 600/529 |
| 2006/0241510 | A1 * | 10/2006 | Halperin et al. | 600/534 |
| 2006/0248652 | A1 * | 11/2006 | Alonso Cucurull | 5/740 |
| 2007/0161917 | A1 * | 7/2007 | Ozaki et al. | 600/529 |
| 2007/0191742 | A1 * | 8/2007 | Park | 600/587 |
| 2008/0052837 | A1 * | 3/2008 | Blumberg | 5/727 |
| 2008/0114260 | A1 * | 5/2008 | Lange et al. | 600/529 |
| 2008/0209641 | A1 * | 9/2008 | Boyd | 5/706 |
| 2008/0275314 | A1 * | 11/2008 | Mack et al. | 600/301 |
| 2009/0006027 | A1 * | 1/2009 | Hinshaw | 702/129 |
| 2009/0177327 | A1 * | 7/2009 | Turner et al. | 700/275 |
| 2009/0240514 | A1 * | 9/2009 | Oexman et al. | 705/1 |
| 2010/0102971 | A1 * | 4/2010 | Virtanen et al. | 340/575 |
| 2010/0317930 | A1 * | 12/2010 | Oexman et al. | 600/300 |
| 2010/0318239 | A1 | 12/2010 | Oexman | |
| 2011/0163859 | A1 * | 7/2011 | Chraime et al. | 340/309.16 |

FOREIGN PATENT DOCUMENTS

| | | | | |
|---|---|---|---|---|
| WO | WO 2008096307 A1 * | 8/2008 | ............ | A61M 21/02 |
| WO | 2009108228 A1 | 9/2009 | | |
| WO | WO 2009108228 A1 * | 9/2009 | ............ | A61M 21/02 |

OTHER PUBLICATIONS

Notification Concerning Transmittal of International Preliminary Report on Patentability (Chapter I of the Patent Coperation Treaty), issued in International Patent Application No. PCT/US2011/022778, dated Aug. 9, 2012; 11 pages.

Written Opinion of the International Searching Authority, issued in International Application No. PCT/US2011/022778, dated Nov. 5, 2011; 10 pages.

\* cited by examiner

SYSTEMS AND METHODS FOR BEDDING WITH SLEEP DIAGNOSTICS

CROSS REFERENCE TO RELATED APPLICATIONS

This application is a CONTINUATION of U.S. application Ser. No. 13/015,399, filed Jan. 27, 2011, which claims the benefit of U.S. Provisional Application No. 61/299,843 filed on Jan. 29, 2010, the entirety of which is incorporated herein by reference in their entireties.

BACKGROUND OF THE INVENTION

Sleep quality is of great interest to many healthcare providers and individuals, since the amount and quality of sleep may affect physical and mental health. Current techniques for quantifying and measuring parameters associated with the quality of sleep for an individual involve sensors mounted on the individual's body, via, for example, a headband or a wristband. Some other techniques involve using remotely mounted sensors such as cameras and microphones to measure these parameters. However, such sensors may be intrusive, as may be the case with headbands or other sensors mounted directly on an individual, or may not be close enough to the individual to collect accurate data, as may be the case with remotely-mounted sensors.

Additionally, sleep quality can be better understood in view of a sleeper's behavior, habits, health, and environment. Sleep quality may be adversely affected by environmental factors such as extreme temperature, too much ambient light, or too high or low humidity. Sleep quality may also be affected by diet, medication, and exercise habits, among other factors. Analysis of sleep quality can provide insight when designing a diet, medication plan, exercise regimen, or sleep environment.

SUMMARY OF THE INVENTION

Accordingly, systems and methods are disclosed herein relating to systems and methods for bedding and/or mattress assemblies with sleep diagnostic systems. In one aspect, the systems and methods described herein relate to a sleep diagnostic system including a mattress assembly, a plurality of sensors, data acquisition circuitry, an input device, a sleep processor, and a display device. The mattress assembly may have a sleeping surface, and the plurality of sensors may be disposed within the mattress assembly below the sleeping surface. The sensors are configured to measure at least one sleep condition and output data signals indicative of the sleep condition. The data acquisition circuitry receives data signals from at least one of the sensors. The input device, which includes circuitry and a graphical user interface, receives input signals from a user. The sleep processor receives signals from both the data acquisition circuitry and the input device, and determines a sleep characteristic based upon these received signals. The display device, which includes circuitry and a graphical user interface, receives the sleep characteristic from the sleep processor and displays it to the user.

The sleep processor may be disposed within the mattress assembly. A mobile device may include the input device and/or the display device. The mattress assembly may include a transmitter to transmit the sleep characteristic determined by the sleep processor to the mobile device for display. The mattress assembly may include a removable cover that houses one or more of the sensors.

Alternatively, the data acquisition circuitry and the sleep processor may be disposed within a mobile device. A transmitter disposed within the mattress assembly may receive data signals from at least one of the sleep sensors and transmit the data signals to the mobile device. The mobile device may also include a locator processor to determine the location of the user and communicate the location to the sleep processor. Using a network interface, the mobile device may retrieve weather information, barometric information, sunrise time, and sundown time from a network based on the location of the user as determined by the location processor. The mobile device may alert the user of a bed time determined in part by the received data signals from the sensors. If the user is determined to be sleeping by the sleep processor, the mobile device may block incoming notifications.

In another embodiment, the sleep diagnostic system includes a decision processor used to generate a recommendation for a user based on the sleep characteristic determined by the sleep processor. This recommendation may also be based on the user input. The sleep processor may be able to receive additional user input from an external database. User input may be related to the user's environment, previous activities, and health.

In another embodiment, the sleep diagnostic system includes a network interface for transmitting data signals and/or a sleep characteristic to a third party. The third party may return a sleep characteristic or a recommendation over a network to the network interface. The third party may be a healthcare service provider or a social networking website.

The sleep diagnostic system may include a database that stores sensor data, sleep characteristics, and/or recommendations. The sleep processor may generate a sleep summary from the data in the database from a time frame greater than 24 hours.

The sleep characteristic may be a length of time in bed, a sleep start time, a sleep end time, a measurement of respiration, or a measurement of moving. The sensors of the sleep diagnostic system may be configured to measure movement, pressure, weight, stress, strain, temperature, humidity, light, noise, heart rate, breathing, blood oxygenation, blood pressure, time in bed, or total time slept. Sensors near the head region may be able to detect breathing. Sensors near the center of the mattress may detect weight. Sensors near the foot of the mattress may detect movement.

In another aspect, the systems and methods described herein relate to a sleep diagnostic method for carrying out the functionalities described above. The method may include waking up the user at a time based on the sensor signal data.

In another aspect, the systems and methods described herein relate to a mattress cover including at least one sleep sensor and at least one wireless transmitter. The sleep sensors may be similar to the aforementioned sleep sensors. The wireless transmitter may transmit the data signals to a sleep processor, which is configured to carry out the functionalities described above.

The mattress cover may also include a padding layer and/or a power source. The mattress cover may be removable and transportable.

BRIEF DESCRIPTION OF THE SEVERAL VIEWS OF THE DRAWINGS

The foregoing and other objects and advantages of the systems and methods described herein will be appreciated more fully from the following further description thereof, with reference to the accompanying drawings wherein.

DETAILED DESCRIPTION OF THE INVENTION

To provide an overall understanding of the systems and methods described herein, certain illustrative embodiments will now be described, including systems and methods for sleep diagnostics. However, it will be understood by one of ordinary skill in the art that the systems and methods described herein may be adapted and modified for other suitable applications and that such other additions and modifications will not depart from the scope thereof.

In many aspects, the systems and methods described herein provide bedding with sleep diagnostics sensors. Since sleep quality is of concern to many individuals, sensors incorporated into bedding may provide useful information related to the sleep quality of an individual. For example, weight or stress/strain sensors may be used to monitor an individual's sleeping position and/or movements during sleep. Similarly, sensors within the bedding may be used to monitor the temperature and/or humidity of the individual's local sleeping environment (e.g., under the covers), which may vary from the overall temperature/humidity of the sleeping environment as a whole (e.g., the bedroom). Sleep diagnostics sensors located within the bedding itself may provide improved accuracy due to proximity to the sleeper, yet also avoid the discomfort associated with other sleep-monitoring systems incorporated into, for example, headbands.

In many aspects, the aforementioned sleep diagnostic sensors may be used in conjunction with additional information about the sleeper's health, lifestyle, and environment in processing the sleep sensor data. Sleep quality may be affected by a sleeper's age, weight, and medical conditions. Furthermore, sleep quality can be affected by a sleeper's lifestyle, such as diet and physical exertion. Additionally, sleep quality can be affected by environmental factors, such as weather and light. Sleep sensor data may be processed in view of these other factors to accurately analyze sleep quality and determine which factors are affecting sleep quality. The sleep diagnostic system may then provide suggestions or recommendations for the sleeper to improve his sleep. In another aspect, the sleep diagnostic sensors may be used in conjunction with a mattress selection application in a mattress showroom to help a customer choose a mattress.

Figure 1:
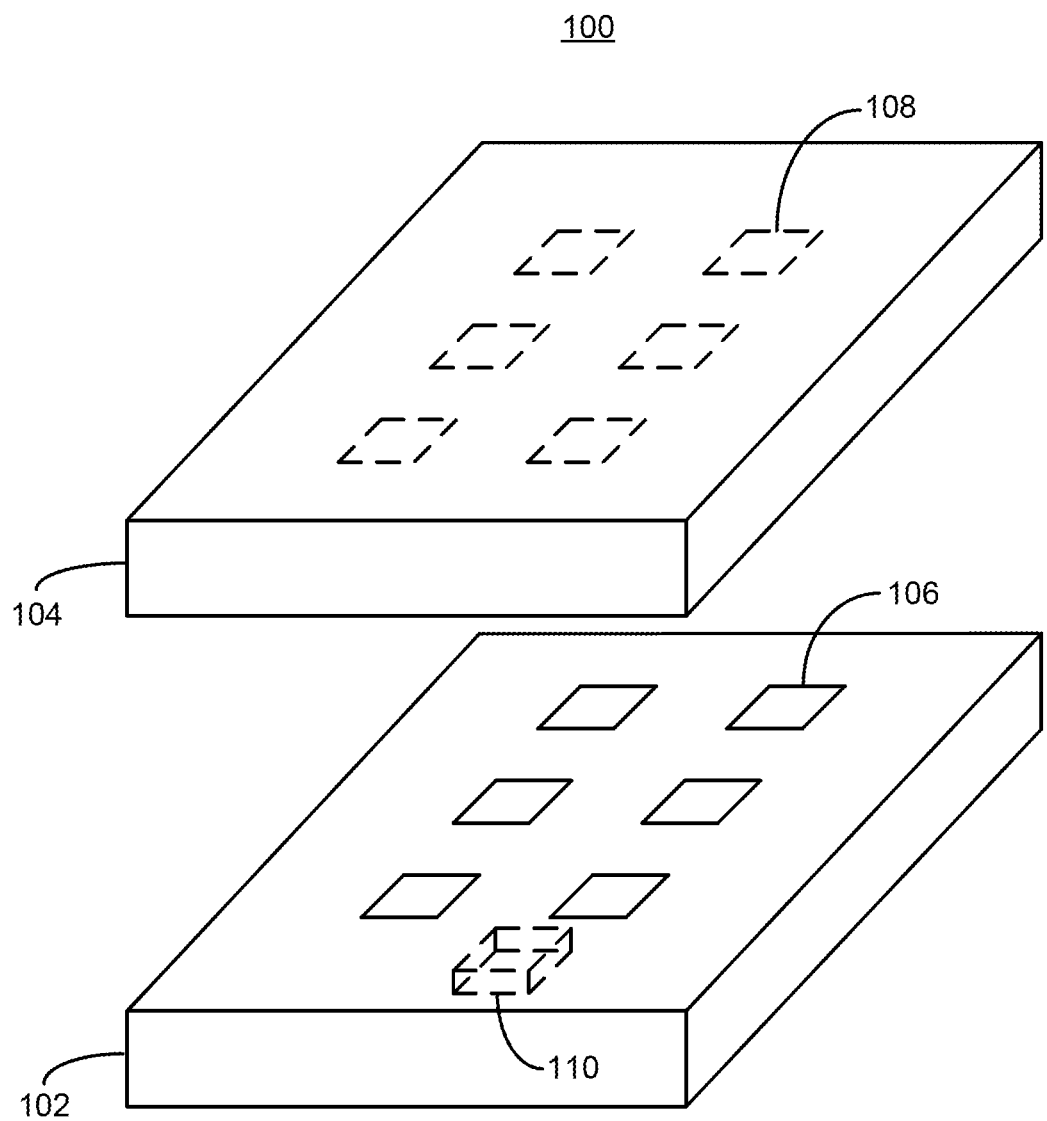
FIG. 1 depicts a mattress assembly with sensors, according to an illustrative embodiment.

FIG. 1 depicts a mattress assembly 100 with sensors, according to an illustrative embodiment. Mattress assembly 100 may include a mattress 104 and a foundation 102. Mattress 104 includes an innercore that may include springs, such as coil springs or encased coil springs. In some embodiments, these springs may be configured to provide foam-like compressive behavior. In certain embodiments, the innercore may include support structures and materials, such as foam, latex, gel, viscoelastic gel, or a combination of the foregoing, in one or more layers. In other embodiments, the innercore may not include any springs. The innercore may have a firmness that varies across its length and width. Foundation 102 may include a mattress frame or mattress corner guards. The mattress frame may be adjustable, allowing the frame and/or mattress to pivot or bend along one or more pivoting axes.

In certain embodiments, mattress 104 may include one or more side rails (not shown). The side rails may be placed on one side of the innercore, opposing sides of the innercore, on three adjacent sides of the innercore, or on all four sides of the innercore. In some mattress embodiments, the innercore may not include springs, and the side rails may include coil or encased coil springs instead. In some embodiments, the springs may be configured to provide foam-like compressive behavior. In certain embodiments, the side rails may include edge supports with firmness comparable to or greater than the firmness of the innercore. The side rails may be fastened to the innercore via adhesives, mechanical fasteners, or any other methods for attachment.

In some embodiments, mattress 104 may include a padding layer. The padding layer may be adjacent to the top surface of the innercore or the bottom surface of the innercore. In some embodiments, mattress 104 may be a reversible mattress, in which the top surface and bottom surface in one configuration may be the bottom surface and top surface, respectively, in another configuration. In certain embodiments with side rails, the side rails may also be constructed in a reversible manner. In other embodiments, there may be a padding layer adjacent to the top surface and another padding layer adjacent to the bottom surface of the innercore. The padding layer may include foam, gel, or any other type of padding material, in one or more layers. In some embodiments, mattress 104 may include a topper pad that may define the top exterior surface of the mattress. This topper pad may include foam gel, or any other type of padding material, in one or more layers. In certain embodiments, the topper pad and/or the padding layer may be made of quiltable material. The topper pad may have a uniform height or thickness along its width and length, or its height or thickness may vary along at least one of the width and length. For example, the topper pad may be thicker in the center than at its periphery. In some embodiments, such as for a reversible mattress, a second topper pad may define the bottom exterior surface of the mattress. In certain embodiments, mattress 104 may include an exterior, removable cover. The exterior, removable cover may encapsulate the entire mattress 104 or only a portion of it, such as, for example, the top portion. The exterior, removable cover may fasten to a portion of mattress 104 or to a portion of foundation 102 via mechanical fasteners such as zippers, buttons, hook and clasp fasteners, ties, or any other fastener or fastening method that allows the cover to be removed and replaced. In some embodiments, the removable cover may fasten to itself instead of or in addition to the mattress 104 and/or the foundation 102.

In certain embodiments, mattress 104 may include one or more fire-retardant, liquid-resistant, or allergy-resistant layers. One or more of these layers may be placed adjacent to the innercore on its top surface, bottom surface, and/or one or more side surfaces. In some embodiments, one or more of these layers may be placed adjacent to a surface of a padding layer or a topper pad in the mattress 104. The one or more fire-retardant layers may comprise a fire barrier fabric or laminate that complies with regulatory requirements for flammability, such as the California Bureau of Home Furnishings Technical Bulletin 129 Flammability Test Procedure, the entirety of which is hereby incorporated by reference. In certain embodiments, a fire-retardant layer may be quiltable. The one or more liquid-resistant or allergy-resistant layers may comprise a coated or uncoated fabric or laminate material. The liquid-resistant or allergy-resistant layer may be breathable and quiltable.

The various layers detailed above may be fastened to each other in a number of ways. For example, layers may be attached to each other along the edges, in the center, between the edges and the center, or some combination of the above. Attachment may be done via stitching, quilting, adhesives, or fastening via mechanical fasteners.

Mattress assembly 100 may include one or more sensors 106 and 108. Sensors 106 and 108 may be incorporated into the foundation 102 and the mattress 104, respectively. Sensors 106 and 108 may be disposed and/or configured to measure parameters that may be related to sleep and sleep quality. For example, sensors 106 and 108 may be configured to measure movement, pressure, weight, stress/strain, temperature, humidity, light, noise, heart rate, breathing, blood oxygenation, blood pressure, time in bed, total time slept, and/or other suitable parameters related to sleep and sleep quality. In some embodiments, one or more of the above parameters may not be directly measured, but rather derived from other measured parameters and/or vital signs (including initial vital signs). Sensors 106 and 108 may be any conventional sensor used to measure any of the above parameters, such as weight sensors, temperature sensors, humidity sensors, microphone/noise sensors, accelerometers, and/or other suitable sensors. In some embodiments, the sensors 106 and 108 may be configured as substantially planar sensors. In these embodiments, the sensors 106 and 108 may be disposed within or on the foundation 102 and/or the mattress 104, as will be described below in relation to FIG. 2. The sensors 106 and/or 108 may be distributed along one or more major or sleeping surfaces of the mattress 104 and/or the foundation 102. For example, noise sensors may be distributed primarily along the head and/or foot (i.e., where the head or foot of an individual sleeping on mattress assembly 100 would most likely be disposed), and weight sensors may be distributed along the length of the mattress assembly, where a sleeping individual would most likely lie. In other embodiments, sensors may be distributed evenly across one or more of the surfaces of the mattress 104 and/or the foundation 102. Optionally, sensors may be disposed in or on a bedframe for supporting foundation 102 and/or mattress 104. In yet other embodiments, sensors may be disposed on or in other bedclothes, such as sheets, comforters, blankets, quilts, pillows, and/or pillow covers.

In some embodiments, the sensors 106 and 108 may be flexible. For example, the sensors 106 and/or 108 may comprise flexible membrane sensors fabricated on a flexible support of plastic or any other suitable, flexible substrate. In certain embodiments, the sensors 106 and/or 108 may include flexible, metallic conductors and/or sensing elements. Incorporating flexible sensors into bedding may improve the comfort of the bedding. However, in some embodiments, conventional, non-flexible sensors may be incorporated into bedding. In these embodiments, the sensors may be disposed beneath one or more layers (see, e.g., FIG. 2), or the sensors may be small enough to avoid significant discomfort.

Mattress assembly 100 may also include an interface module 110, which may be incorporated into the foundation 102 (as shown in FIG. 1) or incorporated into the mattress 104. Interface module 110 may provide a centralized interface for the sensors 106 and/or 108. For example, the sensors 106 and/or 108 may be configured to communicate with interface module 110 via wired or wireless connections. In a wired connection, one or more sensors may be connected via one or more wires to one or more other sensors. In a wireless connection, one or more sensors may have a wireless transmitter and/or receiver for communicating with each other and/or the centralized interface. In some embodiments, the interface module 110 may include processing circuitry to collect, store, and/or process data gathered from sensors 106 and/or 108. In certain embodiments, the interface module 110 may act as an external interface/relay, for linking the sensors 106 and/or 108 with an external processor. In these embodiments, the interface module 110 may communicate via a wired or wireless connection to the external processor. Interface module 110 may include a power supply, both for powering the interface module 110 itself as well as any sensors 106 and/or 108 that may require power. The power supply may be charged via a wired connection with an external charging source, or may be charged via a wireless connection, such as an induction circuit.

In some embodiments, mattress assembly 100 may include one or more actuators (not shown). These actuators may be able to, for example, provide tactile or audio feedback to a user, such as vibrations or noise. For example, the actuators may be configured to play music, provide a massage, or act as a wake-up alarm.

In other embodiments, the interface module 110 may be disposed at a remote location from the mattress assembly 100. The sensors 106 and/or 108 may connect with the interface module 110 via a wireless connection. The interface module 110 may include a computer processor or a remote device such as a cellular phone, personal digital assistant (PDA), smartphone (such as the Apple® iPhone® manufactured by Apple, Inc., located in Cupertino, Calif.). In these embodiments, measurements taken by the one or more sensors 106 and/or 108 may be transmitted to the interface module 110 for processing. In certain embodiments, the interface module 110 may communicate with and operate one or more actuators (not shown) in the mattress assembly 100. These actuators may be configured to, for example, vibrate or move the mattress assembly 100. In some embodiments, these actuators may include one or more audio speakers.

Figure 2:
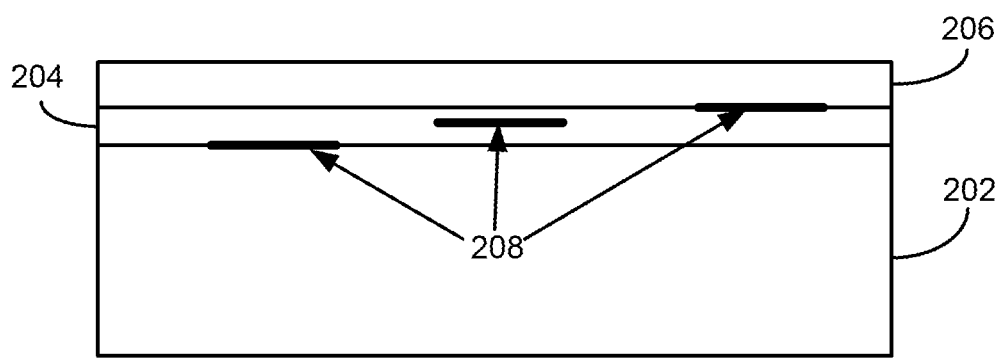
FIG. 2 depicts a cross-section view of a mattress assembly with sensors, according to an illustrative embodiment.

FIG. 2 depicts a cross-section view of a mattress assembly 200 with sensors, according to an illustrative embodiment. Mattress assembly 200 includes a lower layer 202, at least one intermediate layer 204 above the lower layer 202, and an upper layer 206 above the intermediate layer 204. In other embodiments, mattress assembly 200 may include more layers, or fewer layers. In some embodiments, the lower layer 202, the intermediate layer 204, and/or the upper layer 206 may include springs, coil springs, encased coil springs, foam, latex, gel, viscoelastic gel, or a combination of the foregoing, in one or more layers. In certain embodiments, mattress assembly 200 may have other layers above upper layer 206 and/or below lower layer 202. These layers may include topper pads, upholstered pads, border panels, or any such outer fabric or padding layer. The various layers described above may be fastened to each other in a number of ways. For example, layers may be attached to each other along the edges, in the center, between the edges and the center, or some combination of the above. Attachment may be done via stitching, quilting, adhesives, or fastening via mechanical fasteners.

Mattress assembly 200 includes one or more sensors 208. In the illustrated embodiment, one of the sensors 208 is disposed at the interface between the lower layer 202 and the intermediate layer 204, and another sensor is disposed at the interface between the intermediate layer 204 and the upper layer 206. In other embodiments, sensors 208 may be disposed at the interface between any two adjacent layers. Similarly, while one of the sensors 208 shown in FIG. 2 is disposed within intermediate layer 204, sensors may be disposed within any layer. Optionally, different sensors may be disposed at different vertical locations within mattress assembly 200. The vertical location of a particular sensor may be based on its particular characteristic. For example, temperature and/or humidity sensors may be disposed closer to the sleeping surface of the mattress assembly 200 and therefore closer to the sleeping individual, to minimize signal losses due to intervening bedding layers. Weight sensors may not be as susceptible to signal losses from intervening bedding layers, and so may be disposed away from the sleeping surface. In some embodiments, sensors with more flexibility may be placed closer to the sleeping surfaces and sensors with less flexibility may be disposed away from the sleeping surfaces and under more padding, to improve comfort while still collecting data.

The region, such as head region or foot region, a particular sensor is placed in may also depend on its particular characteristic. For example, sensors that measure respiration, such as noise sensors, may be disposed near the head region of the mattress assembly 200 to best detect breathing and snoring. Weight sensors may be disposed in the middle of the bed for detecting the position of the sleeper's torso. Sensors to detect motion may be disposed near the foot of the bed for detecting leg motion indicative of, for example, restless leg syndrome.

Sensors 208 disposed at the interface between two layers may be fastened to one or both layers via, for example, stitching, quilting, adhesives, or fastening via mechanical fasteners. In some embodiments, the sensors 208 may be incorporated into a thin sensor layer (not shown) that may be disposed between two layers. The thin sensor layer may be attached to one or both adjacent layers, via the attaching means described above. In some embodiments, one or more sensors 208 may be incorporated within a mattress layer, such as a padding layer or an upholstery layer. The sensor(s) may be incorporated during the layer manufacturing process.

In certain embodiments, one or more sensors 208 are disposed on the sidewalls of one or more of the bedding layers. One or more sensors 208 may be disposed on the mattress foundation, headboard, and/or footboard. In other embodiments, the sensors 208 may be mounted on a surface of the mattress assembly and extend therefrom. In such embodiments, the sensors 208 may extend towards or away from a user sleeping on the mattress.

Figure 3:
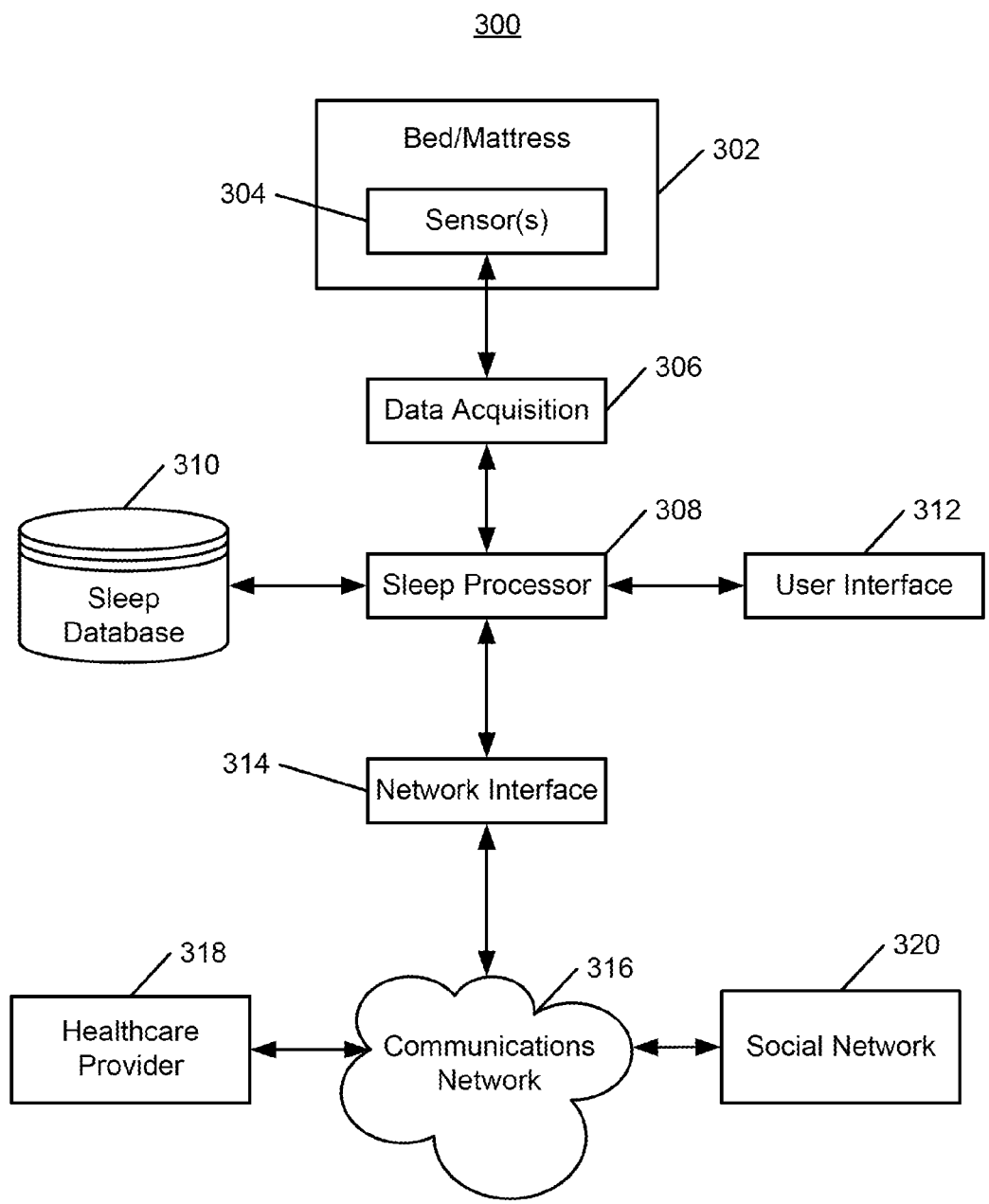
FIG. 3 is a block diagram of a sleep diagnostic system, according to an illustrative embodiment.

FIG. 3 depicts a sleep diagnostics system 300, according to an illustrative embodiment. System 300 includes a bed/mattress 302 with sensors 304. The sensors 304 may communicate with a data acquisition device 306, which communicates with sleep processor 308. The sleep processor 308 is in communication with a sleep database 310, a user interface 312, and a network interface 314. The network interface connects the sleep processor to communications network 316, such as the internet, which may also be in connection with, for example, a healthcare provider 318 and a social network 320.

The bed or mattress assembly 302 may be similar to the mattress assemblies 100 and 200 described with respect to FIG. 1 and FIG. 2, respectively. The sensors 304 may be similar to sensors 106 and/or 108 and 208 described with respect to FIG. 1 and FIG. 2, respectively. The data acquisition device 306 receives electronic signals from the sensors 304 through a wired or wireless connection, e.g. BLUETOOTH, ZIGBEE, WIFI, etc. The data acquisition device 306 may process the received signals, for example through analog-to-digital conversion, domain transform, filtering, or any other signal processing technique or a combination thereof for further processing by the sleep processor 308. Each sensor 304 may be in communication with its own dedicated data acquisition device 306, or there may be a single data acquisition device 306 for receiving signals from all sensors 304. In some embodiments, there may be a data acquisition device 306 for each type of sensor, e.g. a weight data acquisition device for receiving signals from all weight sensors.

The data acquisition device 306 may communicate the received data signals to a sleep processor 308 through a wired or wireless connection. The sleep processor 308 may include microcontrollers and microprocessors programmed to receive data from the sensors 304, and determine sleep parameters based on the received data. In particular, the sleep processor 308 may include a central processing unit (CPU), a memory, and an interconnect bus (not shown). The CPU may include a single microprocessor or a plurality of microprocessors for configuring the sleep processor 308 as a multi-processor system. The memory may include a main memory and a read-only memory. The sleep processor 308 and/or the sleep database 310 may include mass storage devices having, for example, various disk drives, tape drives, FLASH drives, etc. The main memory may include dynamic random access memory (DRAM) and high-speed cache memory. During operation, the main memory may store at least portions of instructions and data for execution by a CPU. In certain embodiments, the sleep processor 308 may include circuitry for an analog-to-digital converter and/or a digital-to-analog converter. The analog-to-digital converter circuitry may convert analog signals received at the sensors to digital signals for further processing by the sleep processor 308. In some embodiments, the sleep processor 308 may include general purpose computer systems used as servers, workstations, personal computers, network terminals, and the like.

In some embodiments, the sleep processor 308 may be incorporated within the bed/mattress 302. For example, the interface module 110 (FIG. 1) may include the sleep processor 308 and data acquisition device 306. In some embodiments, the sleep processor 308 may be external to the bed/mattress, and the sensors 304 may communicate with the sleep processor 308 either directly, if the individual sensors are directly linked to the sleep processor 308, or through a data acquisition device 306 similar to interface module 110 (FIG. 1).

The sleep database 310 may include one or more magnetic disk or tape drives or optical disk drives for storing data and instructions for use by the sleep processor 308. At least one component of the sleep database 310, possibly in the form of a disk drive or tape drive, may store information used for processing signals measured from the sensors 304. The sleep database 310 may also include one or more drives for various portable media, such as a floppy disk, a compact disc read-only memory (CD-ROM), DVD, or an integrated circuit non-volatile memory adapter (i.e. PC-MCIA adapter) to input and output data and code to and from the sleep processor 308.

A user interface 312 may be in wired or wireless communication with the sleep processor 308. The user interface 312 may include output devices, such as a monitor, screen, printer, and/or speakers, and input devices, such as a keyboard, mouse, and/or touchpad, in communication with the sleep processor 308 for programming and/or data retrieval purposes. The user interface may be used to receive data input from the sleeper. User input is described further in relation to FIG. 6. The user interface may also be used to provide a sleep summary and sleep recommendations to the sleeper. This aspect is described further in relation to Figure. In one embodiment, the user interface 312 may be a mobile device, such as a laptop, PDA, or smartphone, or another type of computing device, such as a desktop personal computer. The sleep processor 308 may be included in the mobile device or another computing device in communication with the sensors 304 or data acquisition device 306, but be physically separate from the bed or mattress. Alternatively, the sleep processor 308 may be included in the bed or mattress while the user interface device 312 is physically separate from the mattress or bed. An exemplary mobile device implementation is described in relation to FIG. 4. In one embodiment, the user interface 312 may be a part of the mattress or bed assembly, for example, the user interface may be included in the headboard, footboard, or another element of the bed or mattress 302.

The sleep processor 308 may also be connected to a network interface 314 for data communications. The network interface 314 may be a modem, a network card, serial port, bus adapter, or any other suitable data communications mechanism for communicating with one or more local or remote systems. The network interface 314 may provide a relatively high-speed link to a network 316, such as the Internet. The communication link to the network 316 may be, for example, optical, wired, or wireless (e.g., via satellite, cellular, or WiFi network). Alternatively, the sleep processor 308 may include a mainframe or other type of host computer system capable of communications via the network. The sleep processor 308 may communicate with third parties, such as a healthcare provider 318 and/or a social network 320 via the network 316. In some embodiments, the sleep processor 308 may communicate using an infrared connection, a BLUETOOTH protocol, or any other suitable wireless communication protocol. The sleep processor 308 may also include suitable input/output ports or use the interconnect bus for interconnection with other components, such as user interface 312.

Figure 4:
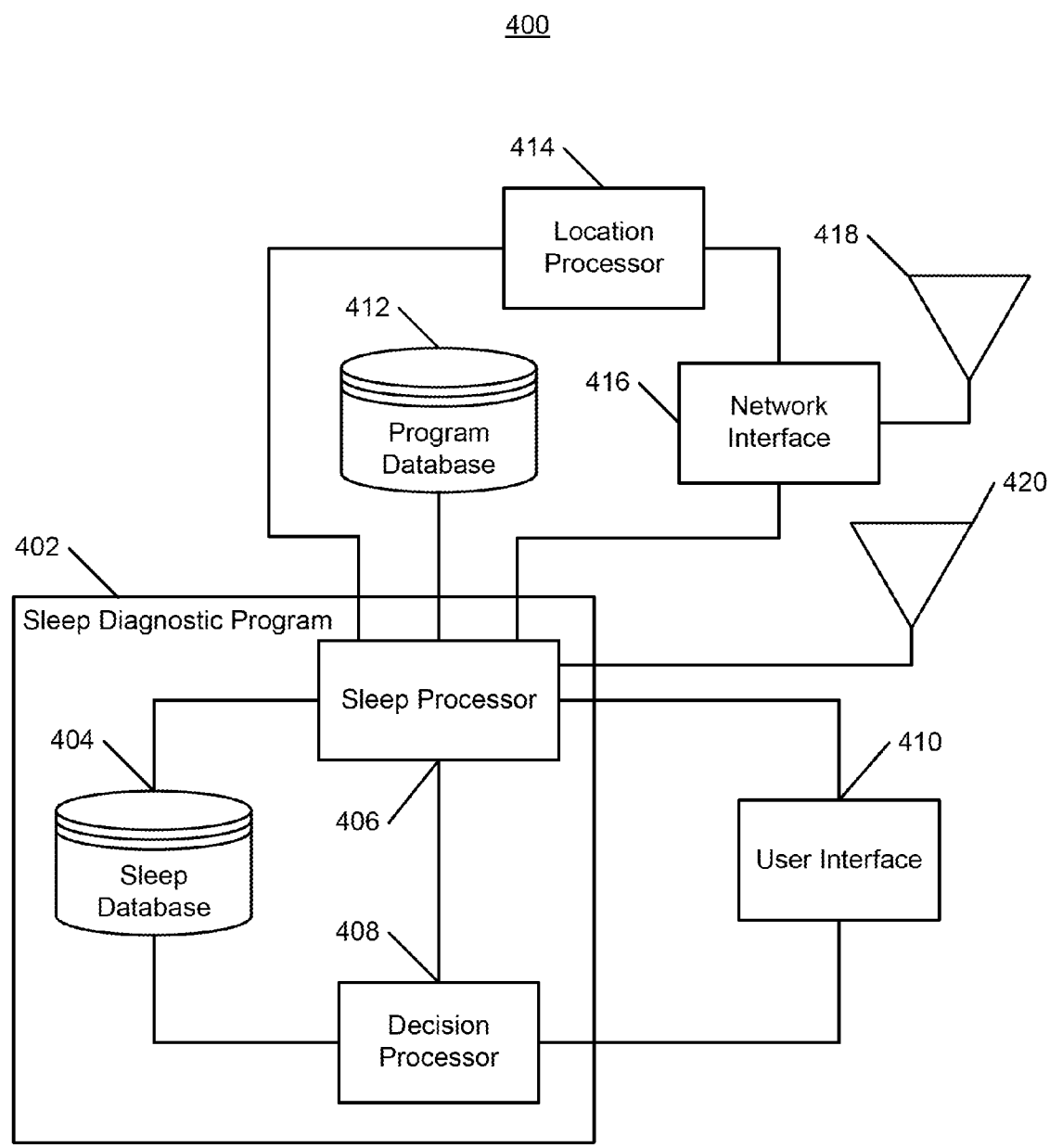
FIG. 4 is a block diagram of a mobile device for use in the sleep diagnostics system of FIG. 3, according to an illustrative embodiment.

FIG. 4 is a block diagram of an exemplary mobile device 400 for use in a sleep diagnostic system. Mobile device 400 includes a sleep diagnostic program 402 including a sleep database 404, a sleep processor 406, and a decision processor 408. Mobile device 400 may include a user interface 410, at least one program database 412, a location processor 414, and a network interface 416. The network interface 416 may be connected to antenna 418. The mobile device may include one or more additional antennas 420 in communication with one or more components of mobile device 400 described above.

The mobile device 400 may be a cell phone, smart phone, laptop, notebook, tablet computer, palm-sized computer, or any electronic device capable of receiving sleep signal data, accepting user input, processing data, and providing an output to a user. The mobile device 400 may be configured to run one or more applications, including sleep diagnostic program 402.

The sleep processor 406 is connected to sleep database 404, which is similar to sleep database 310 of FIG. 3. The sleep diagnostic program 402 may include a decision processor 408 which uses the output of the sleep processor to determine advice or a recommendation for a sleeper based on his sleep data. Recommendations will be discussed further in relation to FIG. 5 and FIG. 7. A general purpose processor of the mobile device 400 may be considered a decision processor 408 when processing sleep signal data to determine a recommendation. The sleep processor 406 and decision processor 408 are connected to a user interface 410. The user interface 410 may include a keypad, keyboard, microphone, screen, touch screen, or speaker. The user interface 410 is configured to receive input from a user, particularly through question or surveys. The user interface 410 is also configured to output the results of the sleep diagnostic program, such as sleep summary data and recommendations, to the user. The user inputs and outputs of the sleep diagnostic program are discussed further in relation to FIGS. 6 and 7, respectively.

The sleep processor may be in communication with one or more program databases 412. These databases may store user data for other applications on the mobile device 400. The user data may be useful to the sleep processor 406. The program databases 412 may also be in communication with the decision processor 408 (connection not shown). An exemplary program database 412 is the database of a diet tracking application. An individual's sleep quality may be affected by a user's food choices. For example, if a user eats a spicy or greasy dinner, he may experience gastroesophageal reflux, i.e., acid reflux, making it difficult for the user to fall asleep or cause episodes during the night rousing the sleeper. If an individual eats foods with high tryptophan content, he may fall asleep faster than had he eaten lower tryptophan foods. Program databases 412 may also include, for example, the database of a prescription reminder application, as the medications an individual takes may favorably or adversely affect sleep quality, or the database of an exercise tracking application, as the amount of physical exertion may favorably or adversely affect sleep quality.

The sleep processor is also connected to a location processor 414 which may use any suitable geolocation technique to determine the location of the sleeper. The location processor 414 may process, for example, global positioning satellite (GPS) signals, cell phone tower signals, or IP network addresses. The sleeper's location may be used, for example, to determine local weather data, barometric data, sun-up or sun-down times, or other location-based data which may influence an individual's sleep quality. The sleeper's location may also be used to determine if an individual is sleeping at home, at another residence, in a hotel, in a car or recreational vehicle, on an airplane, or in another type of location.

The location processor 414 and sleep processor 406 are connected to a network interface 416 for connecting to, for example, a cellular data network or a WIFI network via an antenna 418. The sleeper's location and environmental data associated with the location may be retrieved from a network accessed via the network interface 416 and the antenna 418. The sleep processor 406 may also retrieve additional information related to the sleeper from a network, such as online databases for food, medication, and exercise tracking similar to those discussed in relation to the program database 412. The network interface 416 may be used to connect to a social networking website, allowing a user's status and sleep data to be automatically uploaded to the social networking website. Additionally, the network interface 416 may be used to send data to a healthcare services provider or sleep specialist, who may examine the received sleep data for sleep quality diagnosis or other health related examination.

The network interface 416 may be used to receive sleep data signals directly from the sleep sensors 304 or from data acquisition device 306 if the data is sent using, for example, WIFI protocol. On the other hand, the sleep signal data may be sent using a different protocol, such as BLUETOOTH or ZIGBEE, which may use a different antenna 420 that may not require a network interface.

Figure 5:
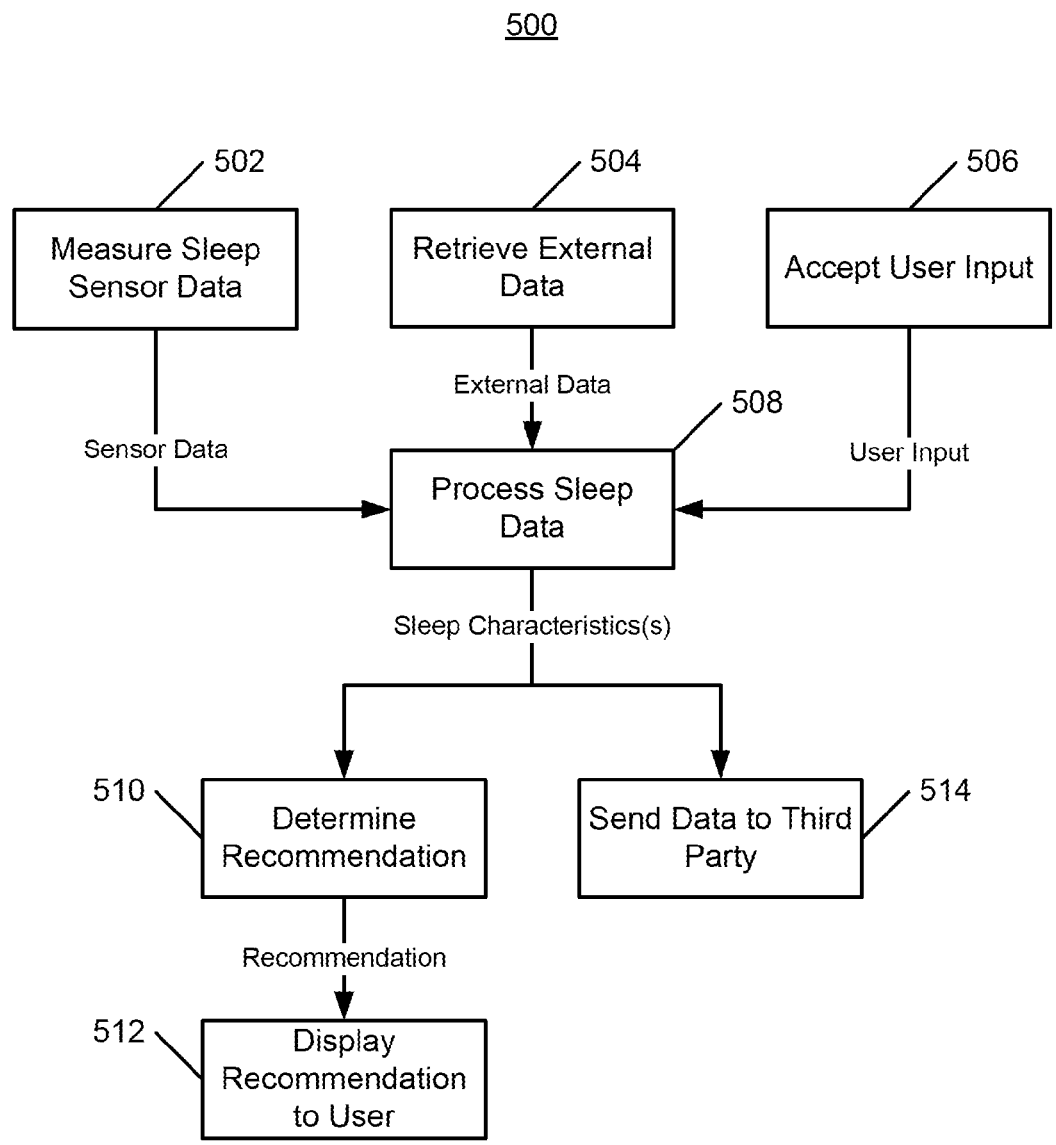
FIG. 5 is a flowchart depicting a process for sleep diagnostics, according to an illustrative embodiment.

FIG. 5 is a flowchart depicting a process 500 for sleep diagnostics, according to an illustrative embodiment. The sleep diagnostics process 500 includes receiving at least three inputs: data from sleep sensors (step 502), external data (step 504), and user input (step 506). These inputs are then processed (step 508) to determine at least one sleep characteristic. From the sleep characteristic, a recommendation is determined (step 510) and displayed to a user (step 512). Additionally, sleep characteristics or other sleep data may be sent to a third party (step 514).

In step 502, data parameters reflective of sleep quality for a user may be collected by, for example, sensors 106 and/or 108 (FIG. 1). These parameters may include weight data, stress/strain data from sensors such as strain gages, temperature, humidity, and noise. These collected parameters may then be transmitted to, for example, sleep processor 308 (FIG. 3).

In step 504, external data, which refers to data stored outside of the sleep database, is retrieved at the sleep processor 308 from sources such as the location processor 414 (FIG. 4), program databases 412 (FIG. 4), and networks such as the internet. The external data may relate to the sleeper's health, behaviors, activities, or environment. In step 506, the user interface 410 (FIG. 4) accepts user input, which may include information about the sleeper's health, behaviors, activities, or environment, or other information, such as a user's preferred alarm settings.

In step 508, the collected information may be processed to determine one or more sleep characteristics by the sleep processor 308. In some embodiments, the sleep processor 308 may combine time data collected from an internal clock associated with the sleep processor 308 (or the sensors 304) with the sensor data. Thus, the amount of time a user spent in bed may be determined by determining the time at which a weight sensor detects a significant increase in weight and the time at which the weight sensor detects a significant decrease in weight. Similarly, instances where the user gets up to, for example, get a drink of water or use the bathroom, can be determined. Noise sensor data combined with time data may be used to determine the onset of sleep and wakefulness by, for example, measuring breathing frequency. Sleep problems may be reflected by loud noise data while the user is in bed, or by rapid fluctuations in bedding weight or stress/strain sensors, which may indicate movement during sleep (i.e., tossing and turning). Environmental sensors such as temperature, humidity, and light sensors may provide data about the local sleeping environmental conditions for a particular user.

One or more sleep behaviors and events may be analyzed in view of data from the environmental sensors, external data, and user input. External data and user input are helpful in determining the causes of sleep behaviors and events. For example, the individual indicates that he had several glasses of water before going to bed, getting up can be attributed to going to the bathroom, whereas if the user indicates that he did not drink very much that day, getting up may be attributed to getting a drink of water. If the user changes habits and behaviors, such as exercise habits, diet, pre-bed rituals such as reading or watching TV, allowing pets to sleep in the user's bed, etc., the sleep diagnostic program can analyze how these actions affect sleep patterns, and determine to which cause to attribute sleep characteristics. The sleep diagnostic program can analyze the effects of medications on the individual's sleep patterns, which can help the individual or his physician determine most suitable medications and dosages. If the user changes his thermostat setting the sleep diagnostic program can determine an optimal room temperature or temperature range for sleeping.

Furthermore, if two people share a bed, a single sleep diagnostic program may receive sensor data, external data, and user inputs for either or both parties. The sleep diagnostic program could examine the individuals' sleep quality, personal information, and environmental data to generate a recommendation suitable for both sleepers. For example, if one sleeper prefers a high temperature setting while the other prefers a low temperature setting, the sleep diagnostic program could weigh the preferred temperatures and relative importance of temperature settings to sleep quality for the sleepers to determine an optimal temperature setting. The aforementioned techniques for processing sleep data in view of external data and user settings are meant to be exemplary and are in no way limiting.

The sleep processor 308 may use the collected sleep data to generate feedback for the user about his or her sleep quality. Such feedback may include quantitative data, such as actual sleep time, temperature, humidity, and light level. The quantitative data may be displayed, for example, as the quantitative data itself, as a score or rating based on the quantitative data, or as a graph. The feedback may also include identification of potential problems and recommendations (step 510). For example, if the data indicates that the user is getting up frequently because he drank a lot of water before bed, the sleep processor 308 may determine that the individual should drink less water before going to bed. Similarly, if the sleep processor 308 detects significant noise during sleep indicative of snoring and movement associated with the snoring, the sleep processor 308 may determine that the user should visit a doctor to evaluate the possibility of sleep apnea. Other recommendations may produce from observations and analysis including but not limited to those discussed in relation to step 508.

The sleep processor 308 may communicate the sleep characteristics and/or recommendations to the user (step 512). For example, the sleep processor 308 may transmit quantitative data and/or recommendations, as described above in relation to steps 508 and 510. For example, the sleep processor 308 may provide a user's sleep parameter information and feedback and suggest a course of action, like drinking less water or visiting a doctor. In other embodiments, the sleep processor 308 may communicate more interactively with the user. For example, the sleep processor 308 may inform the user of the time that he/she woke up, and ask if they wish to wake up at the same or a different time the following morning. The sleep processor 308 may then set up an alarm based on the user response. In some embodiments, the sleep processor determines an appropriate bed time for the user based on the past night's sleep quality or multiple nights' sleep quality and the user's wake up time. For example, if a user has a restless night and does not get a sufficient amount of sleep, the sleep processor may set up an alert reminding the user to go to bed early the following night. The alert may only be transmitted to the user when it is determined using, for example, the location processor, that the user is near his home or in the vicinity of his bed. If the user is away from home, an alert could be given to the user at a time before the recommended bed time based on the user's current location so that the user has time to get home and get ready for bed by the recommended bed time.

In some embodiments, the sleep processor 308 may process the sleep data with information in the sleep database 310. In some embodiments, the collected sleep data may be stored to provide historical sleep data for the user, possibly to be sent to a sleep specialist for evaluation. In determining patterns over a multitude of days, data may be adjusted to account for unusual factors. For example, if an individual has a particularly restless night, but had eaten a large, spicy meal while on vacation, this night may not be indicative of his normal sleep patterns. In other embodiments, the sleep processor 308 produces summary reports based on historical data from, for example, the past week, the past month, or from all available data. Summary reports can be generated at regular times, such as once a week or once a month, and/or at the request of the user.

In some embodiments, the collected sleep data may be communicated, either after acquisition or in real time, to third parties (step 514). The sleep data may be sent for evaluation to third parties, including but not limited to doctors, insurance companies, hospitals, and/or databases containing electronic medical or health records. The evaluating third party may then generate summaries or other information, recommendations, or appointments based on the sleep data. This information can be transmitted to the user through the sleep diagnostic program or through another means of communication, such as telephone, mail, or email. In certain embodiments, the collected sleep data may be communicated either directly from the sleep processor 308 or by the user to social networking systems and websites such as Facebook®, Myspace®, and/or Twitter®. The social networking system could alert friends, family, or others that the individual is sleeping and should not be disturbed. Any other information received or determined by the sleep diagnostic system could be posted to a social networking system or website and shared publicly or privately.

In a different embodiment of the process 500 shown in FIG. 5, the sleep diagnostic system described with respect to FIGS. 1-4 may be used to take measurements related to people laying but not necessarily sleeping on the mattress assembly. For example, the system may be used to help a consumer in a store decide which mattress is best considering the consumer's weight, weight distribution, physical condition, mattress preferences, and/or other factors. In this embodiment, a consumer or a sales representative uses a mattress selection application for bed selection. The mattress selection application may be run on a mobile device, personal computer, or any electronic device containing a sleep processor 308 and capable of receiving data, accepting user input, processing data, and providing an output to a user.

In step 502, the sleep sensors measure data such as the weight or pressure of the consumer, the consumer's heart rate, his respiration, or other physical factors, which are sent to the sleep processor 308. In step 504, external data, such as characteristics of mattresses (e.g. overall firmness, firmness zones, plushness, materials, size and price) and their availability, is retrieved and also sent to the sleep processor 308. In step 506, user input, which may include the consumer's preferences in a mattress (e.g. overall firmness, firmness zones, plushness, materials, size and price), physical condition (e.g. weight, body type, age, back or neck pain, arthritis, fibromyalgia, sleep apnea) and sleep behaviors (e.g. back, stomach, or side sleeper; sleep alone or with a partner), is entered.

In step 508, the sleep processor 308 analyzes the sensor input, user input, and sleep sensor data to determine a sleep characteristic, which in this case relates to how suitable a particular mattress is for a consumer. The sleep characteristic may include qualitative or quantitative data, ratings, scores, or grades. In step 510, based on the sleep characteristic, the sleep processor can make a recommendation of which bed or beds would be most suitable for the customer. In step 512, the device running the mattress selection application or another device with a visual output can display the recommendation, along with any other information related to the mattress or sleep characteristic including qualitative or quantitative data; a score, rating, or grade based on the data; or a graph, chart, or other visual representation. The output may be viewed by the customer, a sales representative, or a sales supervisor. In one embodiment for dynamic mattress selection, a mattress selection application first analyzes only the consumer input and/or external data, which directs the consumer towards particular mattresses in the showroom which may be most suitable. The consumer then may test out one or more mattresses and enter ratings or other feedback about the mattress or mattresses. This feedback is used to better refine the recommendations and possibly recommend different mattresses for the consumer to try. In step 514, data may be sent to a third party, such as a sales representative, a sales supervisor monitoring a showroom, or a mattress manufacturer.

Figure 6:
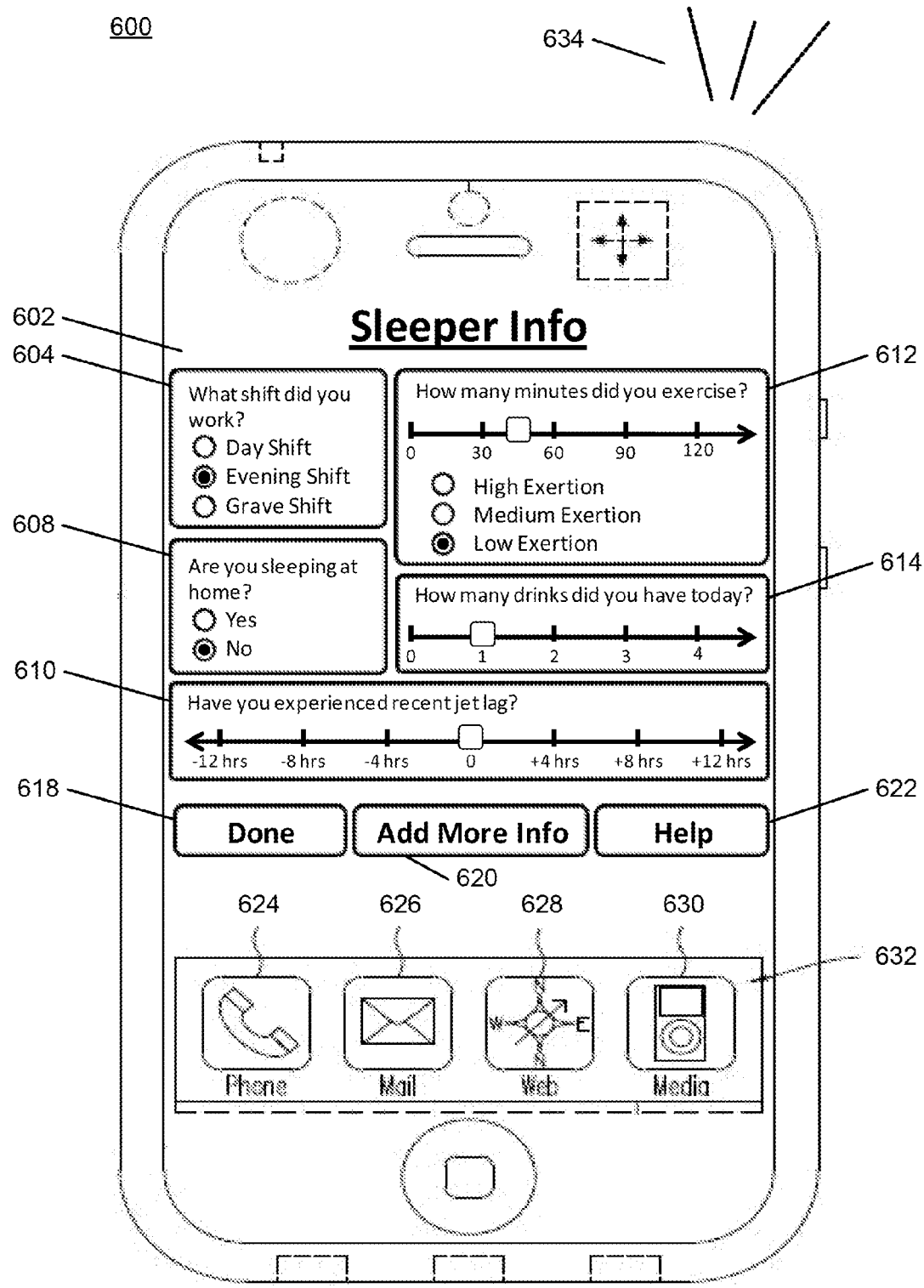
FIG. 6 is a diagram of a mobile device for executing an application allowing user input to a sleep diagnostics system, according to an illustrative embodiment.

FIG. 6 depicts an interactive graphical user interface configured to allow a user to input on a mobile device 600 personal information for use by the sleep diagnostic program 402. As shown, the mobile device can launch one or more applications by selecting an icon associated with an application program. As depicted, the mobile device 600 has several primary application programs 632 including a phone application (launched by selecting icon 624), an email program (launched by selecting 626), a web browser application (launched by selecting icon 628), and a media player application (launched by selecting 630). Those skilled in the art will recognize that mobile device 600 may have a number of additional icons and applications, and that applications may be launched in other manners as well. In the embodiment shown, an application, such as a sleep diagnostic application, is launched by the user tapping or touching an icon displayed on the touch screen 602 interface of the mobile device 600.

As shown, the touch screen 602 displays several questions for the user in boxes 604-614. When the sleeper has entered all of his sleeper characteristics, he may tap the "Done" button 618, which may cause a home or menu screen to display. The questions shown in FIG. 6 for user input of sleeper characteristics are exemplary, and further questions may be accessed by the "Add More Info" button 620. If the user needs any assistance in answering the questions or understanding how to user the sleeper diagnostic program 402, he may tap the "Help" button 622 to view a help menu.

Question 604, which relates to work shift, and question 608, which relates to sleeping location, are asked in a multiple-choice format. The user selects one or, if applicable, more than one response by tapping radio buttons. Question 610, which relates to jet lag, question 612, which relates to exercise, and question 614, which relates to alcohol consumption, is answered by the user moving an indicator along a number line with his finger. In boxes, 612 and 614 for example, if the number line does not go high enough, moving the indicator all the way to the right will cause the numbers on the number line to increase, displaying higher numbers for exercise minutes or number of drinks Box 612 includes both a number line response and a multiple choice response related to exercise. Other types of user input, such as using numerical entry, textual entry, voice recognition, or any other known form of user input may be used.

The questions in FIG. 6 have been shown to effect sleep quality. However, for experimental purposes, questions related to factors not known to be related to sleep quality may be asked. The developer of the sleep diagnostic program or another party can then analyze the results from one or more sleepers and determine if and how a factor affects sleep quality.

Figure 7:
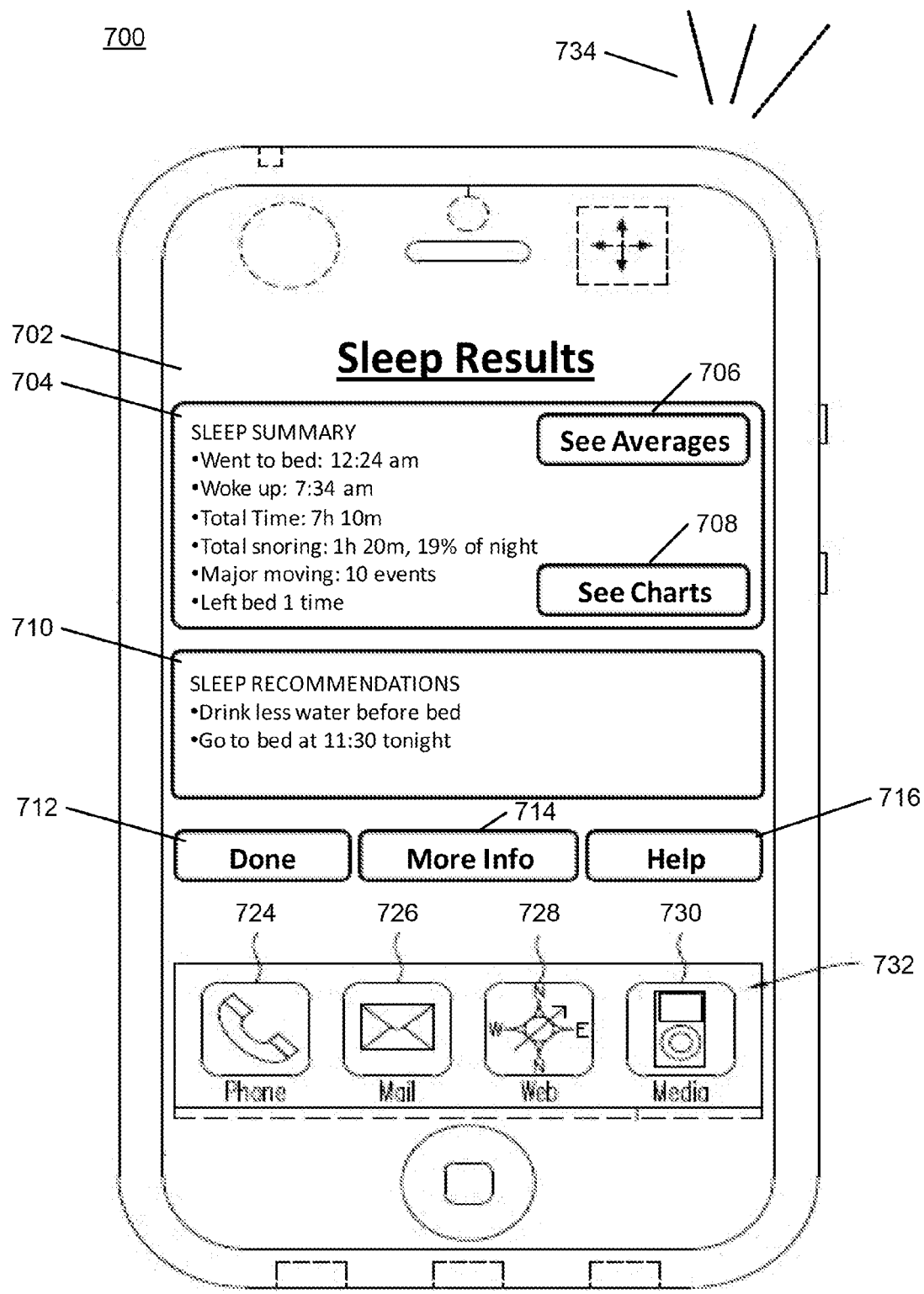
FIG. 7 is a diagram of a mobile device for executing an application providing output from a sleep diagnostics system, according to an illustrative embodiment.

FIG. 7 depicts a diagram of a mobile device displaying the output from a sleep diagnostics system. This screen may be shown to the user after he wakes up or when the user selects a command such as Show Sleep Results from a home or menu page. The results include summary information 704 from the previous night's sleep. As shown, the sleep summary indicates when the sleeper went to bed, when he woke up, the total sleep time, the total snoring time, the number of times the sleeper moved, and the number of times the sleeper left the bed. Any other information related to the sleep quality or sleep environment, as discussed with respect to FIG. 5, may be presented. Additional information can be accessed by tapping the "More Info" button 712. Average sleep data over a time period, such as the past week, the past month, or all available nights, may be accessed by tapping the "See Averages" button 706. Charts summarizing sleep data may be accessed by tapping the "See Charts" button 710.

Any visual representation may be used to display the output of the sleep diagnostics system. For example, visual output may be any combination of numerical, text, and graphical output (e.g. charts, tables, graphs, diagrams, maps, timelines, etc.). The sleep processor 308 or another processing element is able to convert the sleep data and sleep characteristics to graphical output. The user may be able to select data and data ranges to view, and may be able to manipulate the graphical output by, for example, zooming in and scrolling. Buttons, such as the "See Charts" button 710, can be used to select between different modes of visual representation.

In addition, a sleep quality grade or rating (not shown) may be displayed which summarizes the night's sleep quality. Below the sleep summary is sleep recommendations 710. Based on sleep sensor data and all available information from the past night and the user's history, the sleep diagnostic may determine a recommendation as discussed in relation to FIG. 5 and output the recommendation in box 708.

In addition to the output on the mobile device or another user interface and the output sent to third parties, the sleep diagnostic program may also be used to control certain elements of the sleeper's environment. The sleep processor may be connected through a personal area network (e.g. BLUETOOTH or ZIGBEE) or a local area network (e.g. WIFI) to other electrical devices in the sleeper's bedroom. For example, the sleep diagnostic program may control the ambient temperature through connections with a residence's or room's thermostat and/or an electric blanket. If the sleep diagnostic program determines that the sleeper's bed is outside of his optimal sleeping range, the sleep diagnostic program can generate commands to send to the thermostat and/or electric blanket to increase or decrease the ambient or bed temperature, respectively. Similarly, the sleep diagnostic program may receive humidity readings and send control signals to adjust a humidifier or dehumidifier. If the sleeper is using an adjustable bed, the incline may be adjusted to better suit, for example, a snoring sleeper or a sleeper experiencing acid reflux. If the sleeper gets out of bed as determined by weight sensors, the sleep diagnostic program may send a command to a light to turn on. If the sleeper is allergic to his dog and the weight sensors detect that the dog is in bed with the sleeper, the sleep diagnostic program may send a command to a speaker to emit a high pitched noise to awaken and irritate the dog so he may leave. Any other electrical device that may be used to control or alter the sleeping environment may be controlled in a similar manner by the sleep diagnostic system.

In some embodiments, the sleep diagnostic program may control certain elements of the sleep diagnostic system. Actuators embedded in the mattress assembly 100 may provide tactile or audio feedback to a user, such as vibrations or noise, as directed by the sleep diagnostic program. For example, the actuators may be configured to play music, provide a massage, or act as a wake-up alarm. Furthermore, if the user is detected to be sleeping, the sleep diagnostic program may block notification of incoming events, such as phone calls, text messages, or emails, so that the sleeper is not awoken. The sleeper may permit certain notifications, e.g., notifications from certain contacts, even when he is asleep.

Figure 8A:
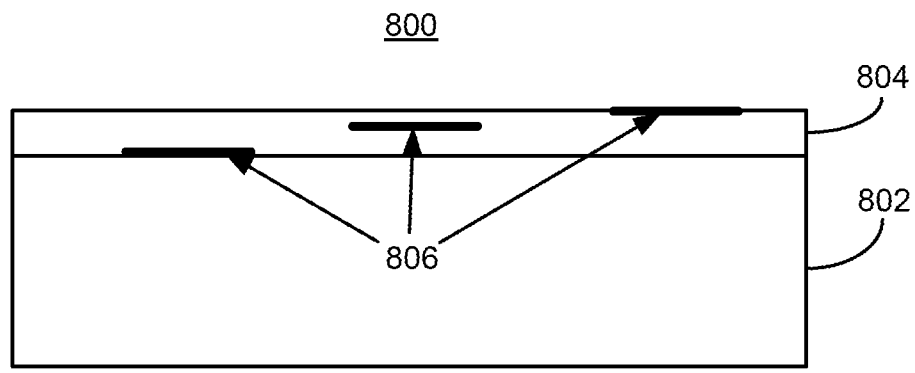
FIG. 8A depicts a cross-section view of a mattress pad with sensors atop a mattress assembly, according to an illustrative embodiment.
Figure 8B:
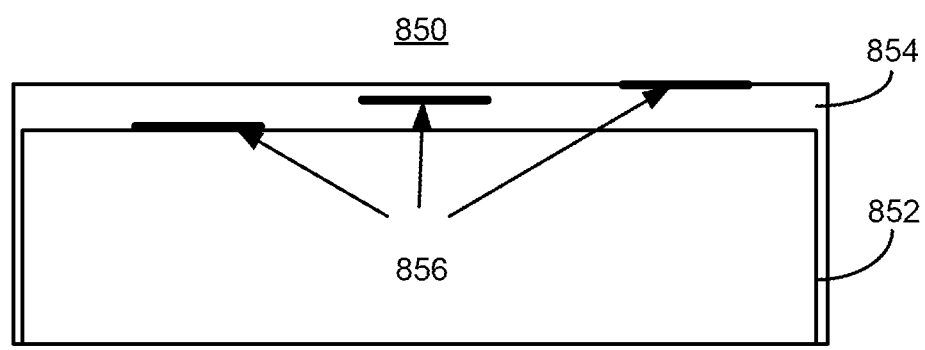
FIG. 8B depicts a cross-section view of a mattress cover with sensors atop a mattress assembly, according to an illustrative embodiment.

FIGS. 8A and 8B depict cross-section views of alternate embodiments of a bed system for sleep diagnostics. FIG. 8A depicts a bed system 800 including a mattress 802, a mattress pad 804, and sleep sensors 806. FIG. 8B depicts a bed system 850 including a mattress 852, a mattress cover 854, and sleep sensors 856. In both FIGS. 8A and 8B, the sensors are not part of the mattress 802 or 852, but rather are included in the mattress pad 804 or the mattress cover 854, respectively, disposed above or around the mattress. The mattress pad or cover includes the sensors 806 and 856 which may be similar to sensors 106 and/or 108 or a subset of these sensors as described in relation to FIG. 1. The mattress pad 804 or mattress cover 854 may also include the interface module 110, power source, and actuators, as described in relation to FIG. 1. The mattress pad or cover may also include foam layers, cloth padding layers, a cloth cover, a fire retardant layer, or any other layer or cover described in relation to FIG. 1. The mattress cover or pad may be sized to dispose on a twin, full, queen, king, California king, or any other mattress size, or the mattress cover or pad may be able to be placed on one or more different mattress sizes by stretching it to fit or folding excess pad around the mattress.

The mattress pad and cover may be removable and transportable. This may allow the mattress pad or cover to be purchased separately from a mattress and placed on any mattress. Furthermore, the mattress pad or cover may be transported from bed to bed, so that a user's sleep quality can be analyzed at more than one location. The mattress pad 804 may be laid on top of a mattress assembly and covered by a fitted sheet. The fitted sheet may hold the mattress pad 804 in place, or it may be secured using Velcro, buttons, zippers, or any other securing means. The mattress cover 854 is fitted over a mattress assembly like a fitted sheet, and may be covered by another fitted sheet for comfort.

Variations, modifications, and other implementations of what is described may be employed without departing from the spirit and scope of the disclosure. More specifically, any of the method and system features described above or incorporated by reference may be combined with any other suitable method, system, or device feature disclosed herein or incorporated by reference, and is within the scope of the contemplated systems and methods described herein. The systems and methods may be embodied in other specific forms without departing from the spirit or essential characteristics thereof. The foregoing embodiments are therefore to be considered in all respects illustrative, rather than limiting of the systems and methods described herein. The teachings of all references cited herein are hereby incorporated by reference in their entirety.

What is claimed is:

1. A sleep diagnostic system, comprising:
    a mattress assembly having a sleeping surface comprising a mattress disposed on a foundation, wherein the foundation is supported by a bedframe that is independent from the foundation;
    a plurality of sensors disposed in contact with and within or within the foundation, wherein the foundation is separate from and underneath the mattress, the plurality of sensors configured to measure at least one sleep condition and output data signals indicative of the at least one sleep condition, wherein the at least one sleep condition comprises at least one of movement, pressure, weight, weight distribution, stress, strain, temperature, humidity, light, noise, heart rate, breathing, and time in bed, and wherein the plurality of sensors are at different vertical locations in contact with and within or within the foundation relative to the sleeping surface depending on the at least one sleep condition measured; and
    an interface module in communication with the one or more sensors, the interface module comprising processing circuitry configured to determine the at least one sleep condition.

2. The sleep diagnostic system of claim 1, wherein the interface module is at a location removed from the mattress assembly.

3. The sleep diagnostic system of claim 1, wherein the interface module is at a location inside the mattress assembly.

4. The sleep diagnostic system of claim 1, wherein the plurality of sensors connect to the interface module via a wireless connection.

5. The sleep diagnostic system of claim 1, wherein the plurality of sensors connect to the interface module via a wired connection.

6. The sleep diagnostic system of claim 1, wherein the mattress assembly further comprises one or more actuators, wherein the interface module communicates with and operates the one or more actuators in the mattress assembly to vibrate or move the mattress assembly or a portion of the mattress assembly.

7. The sleep diagnostic system of claim 1, wherein the interface module comprises a sleep processor and a data acquisition device.

8. The sleep diagnostic system of claim 7, wherein the interface module comprises a sleep processor, a data acquisition device and a radio in wireless communication with the data acquisition device.

9. The sleep diagnostic system of claim 8, wherein the interface module comprises a sleep processor, a data acquisition device and a radio in wireless communication with the data acquisition device that are configured to communicate with a network interface for data communications.

10. The sleep diagnostic system of claim 7, further comprising a user interface in communication with the sleep processor, the user interface configured to receive input data from a user and provide a sleep summary to the user.

11. The user interface of claim 10, where the sleep summary to the user includes one or more of the following metrics: when the sleeper went to bed, when the sleeper awoke, total sleep time, the total snoring time, the number of times the sleeper moved, and the number of times the sleeper left the bed.

12. The sleep diagnostic system of claim 7, wherein the sleep processor is connected to a network interface for data communications.

13. The sleep diagnostic system of claim 7, wherein the data acquisition circuitry and the sleep processor are included within a mobile device.

14. The sleep diagnostic system of claim 7, wherein the sleep processor is a mobile device.

15. The sleep diagnostic system of claim 10, wherein the user interface is a mobile device.

16. The sleep diagnostic system of claim 15, wherein the mobile device is a cell phone, a smart phone, a laptop, a notebook, a tablet computer, or a palm-sized computer.

17. The sleep diagnostic system of claim 14, further comprising a transmitter disposed within the mattress assembly and in communication with at least one of the plurality of sleep sensors for transmitting the data signals to the mobile device.

18. The sleep diagnostic system of claim 15, further comprising a transmitter disposed within the mattress assembly and in communication with at least one of the plurality of sleep sensors for transmitting the data signals to the mobile device.

19. The sleep diagnostic system of claim 15, wherein the mobile device further comprises a location processor configured to determine the location of the user and communicate the location to the sleep processor.

20. The sleep diagnostic system of claim 15, wherein the mobile device further comprises a location processor configured to determine the location of the user on the mattress assembly and communicate the location to the sleep processor.

21. The sleep diagnostic system of claim 15, wherein the mobile device further comprises a network interface for retrieving at least one of weather information, barometric information, sunrise time, and sundown time from a network based on a location of the user.

22. The sleep diagnostic system of claim 15, wherein the mobile device further comprises a sensor to determine ambient noise, temperature, humidity or light.

23. The sleep diagnostic system of claim 15, wherein the mobile device is configured to alert the user of a bed time based in part on the received data signals.

24. The sleep diagnostic system of claim 15, wherein the mobile device is configured to alert the user of a wake time based in part on the received data signals.

25. The sleep diagnostic system of claim 15, wherein the mobile device is configured to block incoming notifications when the sleep processor determines that the user is sleeping.

* * * * *